United States Patent [19]

Walker et al.

[11] Patent Number: 5,166,194
[45] Date of Patent: Nov. 24, 1992

[54] TRANSDERMALLY APPLICABLE PHARMACEUTICAL PREPARATIONS HAVING A PHARMACEUTICALLY USABLE GLYCOSIDE CONTENT

[75] Inventors: Hans Walker, Eschwege, Fed. Rep. of Germany; Karl H. Pegel, Durban Natal, South Africa

[73] Assignee: Roecar Holdings, Curacao, Netherlands

[21] Appl. No.: 652,380

[22] Filed: Feb. 7, 1991

Related U.S. Application Data

[63] Continuation of Ser. No. 399,938, Aug. 29, 1989, abandoned.

[30] Foreign Application Priority Data

Sep. 1, 1988 [DE] Fed. Rep. of Germany ....... 3829640

[51] Int. Cl.$^5$ .................. A61K 31/705; A61K 31/56; A61K 31/45; A61K 31/575
[52] U.S. Cl. ........................................ 514/26; 514/23; 514/969; 514/975
[58] Field of Search .................. 514/23, 26, 969, 975

[56] References Cited

U.S. PATENT DOCUMENTS

| | | | |
|---|---|---|---|
| 2,698,822 | 1/1955 | Halpern et al. | 514/26 |
| 3,639,575 | 2/1972 | Schmolka | 514/171 |
| 4,067,960 | 1/1978 | Fadda | 514/26 |
| 4,146,649 | 3/1979 | Siegel et al. | 514/23 |
| 4,333,926 | 6/1982 | Ohata et al. | 514/23 |
| 4,880,634 | 11/1989 | Speiser | 514/786 |

FOREIGN PATENT DOCUMENTS

| | | | |
|---|---|---|---|
| 2759171 | 12/1979 | Fed. Rep. of Germany | 514/23 |
| 2380030 | 9/1978 | France | 514/26 |

OTHER PUBLICATIONS

Foye, Principles of Medicinal Chemistry (Lea and Febiger, 1981, Philadelphia) p.400.
Geneidi, et al. Egypt. J. Pharm. Sci 1979 (Pub. 1982) 20(1-4) 429-36 Chem. Abs., vol. 97, 1982, Abstract 203171q.
Ackermann et al S. Afr. J. Sci. 1988 84(5) 463-4 Chem. Abs. vol. 109, 1988 Abstract 104095.
Ehrhart, Arzneimittel Entwicklung Wirkung Darstellung, vol. 2, (VCH, Gutenburg 1980) p. 215.

*Primary Examiner*—Robert T. Bond
*Assistant Examiner*—E. C. Ward
*Attorney, Agent, or Firm*—Cushman, Darby & Cushman

[57] ABSTRACT

The invention relates to novel transdermally applicable pharmaceutical preparations containing glycosides; a solvent selected from the group consisting of ethoxylated sterols and ethoxylated alcohols with 12 to 30 carbon atoms; and lipophilic ointment base.

6 Claims, No Drawings

TRANSDERMALLY APPLICABLE PHARMACEUTICAL PREPARATIONS HAVING A PHARMACEUTICALLY USABLE GLYCOSIDE CONTENT

This is a continuation of application Ser. No. 07/399,938, filed on Aug. 29, 1989, which was abandoned upon the filing hereof.

FIELD OF THE INVENTION

The invention relates to novel transdermally applicable pharmaceutical preparations having a pharmaceutically usable glycoside content.

BACKGROUND OF THE INVENTION

There is a very large number of important pharmaceutical products in the form of glycosides, which as a rule are effective only in this form, while their aglycons have lesser or different effects. Among the often used, medically effective glycosides are, for example, the cardioactive glycosides occurring in types of adonis, digitalis, nymphea, nerium, strophanthus, convallaria or urginea. It has long been known that such glycosidic active ingredients often have an improved or at least a more balanced effect if they are administered not in the pure form, but in the form of plant or animal extracts. From this it has been surmised that accompanying substances of natural material are most likely active as carriers; however, it has been very difficult or, in some cases impossible, up to now to determine exactly which substances are acting as carriers here. In any event, with isolated or artificially produced glycosides it has often been shown that the absorption ability is less in comparison with plant extracts, so that some of these glycosides cannot be used for therapy at all or only to a small extent. For example, it is known that in oral applications digitoxin is 100% absorbed, lanatoside A 70%, lanatoside C only 40%, G-strophanthin 2% and gitoxin not at all. In certain cases it has also been attempted to bypass the absorption through the gastro-intestinal tract and to take in the active ingredients through the skin. In those cases where the active ingredients are glycosides, absorption is as a rule insufficient, while with other active ingredients it often is quite good.

Surprisingly, it has now been determined that it is indeed possible to increase the transdermal absorption of glycosidic active ingredients, if the active ingredients are administered together with ethylene oxide adducts having approximately 20 to 30 ethylene oxide units of sterols or alcohols with approximately 12 to 30 C-atoms.

It could not be anticipated that it would be possible to dissolve the glycosides, which as a rule are hard to dissolve not only in water but as a rule even in lipophilic solvents, in an oil phase with the aid of solubilizer and to cause it to absorb transdermally from that phase, even if it is in the form of an emulsion, and this with much higher absorption than so far has been possible by the oral or transcutaneous route.

SUMMARY OF THE INVENTION

According to the invention the active ingredients are mixed together with ethoxylated sterols or ethoxylated alcohols with approximately 12 to 30 C-atoms and are dissolved under slight heating in multivalent alcohols such as 1,2-propanediol or glycerine. All ethoxylated substances can be used as solubilizers and carriers during the subsequent transdermal absorption, either in mixture or as mono-compounds. Among the suitable sterols are, for example, sitosterols, cholesterol, stigmasterol and the naturally occurring mixtures of different sterols such as are found, for example, in the non-detergent (unsaponifiable) fatty matter of fatty oils. Examples of alcohols with approximately 12 to 30 C-atoms that can be used include not only fatty alcohols, but also naturally occurring branched, alicyclic or aromatic alcohols, in particular, such as squalene or phytol derivatives, for example. Some of these compounds, which are easily prepared by reacting the free alcohols with ethylene oxide, are the products already sold by the firm Henkel KGaA under the name "Generol E". These are mostly sitosterol mixtures having a degree of ethoxylation of 20 to 30. An ethoxylated sitosterol having a chain length of 25 EO units is preferably used.

The solutions of the glycosides used as active ingredients in solubilizers and multivalent alcohol in turn dissolve clearly in oil or melted fats. In this case the customary ointment bases are used, such as, for example, mid-chain triglycerides, glycerine monostearate, lanolin, lard, etc. It was a complete surprise to learn that after working the active ingredients into the fatty bases, it was possible to further process them into emulsion ointments, because the mixture is readily emulsifiable with approximately an equal amount of water. Regardless of whether the active ingredients are present in a fatty base free of water or containing water, tests with an active ingredient tagged with $^{14}C$, have shown that penetration into the skin and permeation take place at an approximately five-fold order of magnitude. The active ingredients not only penetrate the skin, but even permeate through the skin so that it is possible, with applications over large surfaces, to attain plasma levels of a height impossible to reach via the intestinal route.

The average composition for transdermal application is approximately 0.01 to 0.1% active ingredients, 1% EO adducts and 10% multivalent alcohol. After dissolving the active ingredient in the mixture of adducts and multivalent alcohol, the clear solution is either mixed with an equivalent amount of water-free ointment base or, in a manner known per se, mixed with approximately half that amount of ointment base, compounded with water with the addition of the customary amount of non-iogenic emulsifiers and emulsified while being stirred with the remainder in the usual manner.

DETAILED DESCRIPTION

The invention will be described in detail below by means of the examples.

EXAMPLE 1

100 mg acetyldigoxin are dissolved with heat in 10.0 g ethoxylated soybean sterol (25 EO units) and 100 g 1,2-propanediol. The solution is heated to approximately 70° C. and then dissolved in a melt, also heated to 70° C., of 100.0 g cetyl palmitate, 350 g stearyl heptamoate, 100 g sorbitan monostearate and 60.0 g PE-sorbitan monostearate. Distilled water at the same temperature is added with intense stirring until a total weight of 1,000.0 g is reached and finally the emulsion is stirred until cold.

EXAMPLE 2

In a melt kept at 70° C. made of 300.0 g hydrated coconut oil, 50.0 g mid-chain triglyceride, 120 g glycerine monostearate and 80.0 g ethoxylated palmityl stearyl alcohol (25 EO units), a mixture of 10.0 ethoxylated soybean sterol (25 EO units), 100.0 g 1,2-propanediol and 20 mg K-strophanthin is stirred in and this mixture is subsequently filled to a weight of 1,000.0 g with water kept at 70° C. The emulsion is slowly stirred until cold.

EXAMPLE 3

Measurements of Penetration or Permeation

Male rabbits approximately 10 weeks old having a body weight of approximately 2 kg were used as test animals. 1.0 g ointment with a radioactivity of 20 μCi of the glucoside tagged with (-C-4) is applied on a shaved area of 10×5 cm on the back of a rabbit, covered with aluminum foil and fixed with a waterproof adhesive strip. After 24 hours the rabbits are sacrificed and the application area is washed several times with swabs moistened with ethanol. The radioactivity of the occlusive dressing material and of the swabs is measured after extraction with ethanol. The skin of the application area is treated with 2 mg lye/methanol/triton×405 (6:3:1 v/v) at 55° C. for 24 hours and then is washed with ethanol heated to 40° C. The radioactivity, measured with a liquid scintillation counter (Philips PW 4700), is a measurement of the penetration in percent of the applied amount of the substance. Permeation in the course of 24 hours is calculated as follows: 100%−(activity of the washing solution+activity of the penetrating amount)=% of penetration. In this test the values for penetration of digoxin were 2.1% of the applied dosage and for permeation were 10.2% of the applied dosage.

EXAMPLE 4

Corresponding to Example 3, the penetration and permeation of $^3$H-ouabain were measured.

In this test the average values for ouabain for penetration were 1.1% of the applied dosage and for permeation 55.4%. Considering the fact that peroral absorption of strophanthins is very low, this high transcutaneous absorption was very surprising and yields entirely novel possibilities for the medical use of strophanthins.

What is claimed is:

1. Transdermally applicable pharmaceutical preparations comprising:
    a pharmaceutically effective amount of glycosides;
    a solvent selected from the group consisting of sitosterol with approximately 25 ethylene oxide units and ethoxylated alcohols with 12-30 carbon atoms; and
    a water containing lipophilic ointment base.

2. Transdermally applicable pharmaceutical preparations comprising:
    a pharmaceutically effective amount of glycosides;
    a solvent selected from the group consisting of squalene derivatives and phytol derivatives; and
    a water containing lipophilic ointment base.

3. A method of administering a pharmaceutically effective amount of glycosides, which comprises:
    applying to the skin a pharmaceutical preparation including
        a pharmaceutically effective amount of glycosides,
        a solvent selected from the group consisting of ethoxylated sterols and ethoxylated C12-C30 alcohols, and
        water containing lipophilic ointment base,
    wherein said glycosides penetrate said skin in an amount ranging from 1.1-2.1% of the applied amount.

4. The method of claim 3 wherein said glycosides permeate said skin in an amount ranging from 10.2-55.4% of the applied amount.

5. The method of claim 3 wherein said glycoside is a digoxin.

6. The method of claim 3 wherein said glycoside is a strophanthin.

* * * * *